United States Patent
Paul (10) Patent No.: US 10,646,535 B1
(45) Date of Patent: May 12, 2020

(54) MODULATING THE ENDOCANNABINOID SYSTEM TO ACHIEVE DESIRED HEALTH OR WELLNESS EFFECTS

(71) Applicant: GnuPharma Corp, Owasso, OK (US)

(72) Inventor: Charles William Paul, Tulsa, OK (US)

(73) Assignee: GnuPharma Corp., Owasso, OK (US)

( * ) Notice: Subject to any disclaimer, the term of this patent is extended or adjusted under 35 U.S.C. 154(b) by 405 days.

(21) Appl. No.: 15/452,254

(22) Filed: Mar. 7, 2017

Related U.S. Application Data (63) Continuation of application No. 15/442,411, filed on Feb. 24, 2017, now abandoned.

(60) Provisional application No. 62/301,219, filed on Feb. 29, 2016.

(51) Int. Cl.

| | |
|---|---|
| *A61K 36/8962* | (2006.01) |
| *A61K 36/48* | (2006.01) |
| *A61K 36/537* | (2006.01) |
| *A61K 36/484* | (2006.01) |
| *A61K 36/77* | (2006.01) |
| *A61K 36/31* | (2006.01) |

(52) U.S. Cl.
CPC .......... *A61K 36/8962* (2013.01); *A61K 36/31* (2013.01); *A61K 36/48* (2013.01); *A61K 36/484* (2013.01); *A61K 36/537* (2013.01); *A61K 36/77* (2013.01)

(58) Field of Classification Search
CPC .... A61K 36/8962; A61K 36/31; A61K 36/48; A61K 36/484; A61K 36/537; A61K 36/07
See application file for complete search history.

(56) References Cited

PUBLICATIONS

Reynoso-Moreno I., et al "An Endocannabinoid Uptake Inhibitor from Black Pepper Exerts Pronounced Anti-Inflammatory Effects in Mice" J. Agric. Food Chem. Sep. 24, 2017, 65(43), pp. 9435-9442: DOI: 10.1021/acs.jafc.7b02979. (Year: 2017).*

Thors, L. et al., Biochanin A, a naturally occurring inhibitor of fatty acid amide hydrolase, British Pharmacological Society, Br J Pharmacol, Jun. 2010; 160(3): 549-560.

Bahi, A., et al., B-Caryophyllene, a CB2 receptor agonist produces multiple behavioral changes relevant to anxiety and depression in mice, Physiol Behav, Aug. 2014; 135: 119-24, Epub Jun. 13, 2014.

* cited by examiner

*Primary Examiner* — Aaron J Kosar
(74) *Attorney, Agent, or Firm* — McAfee & Taft (57) ABSTRACT

Formulations and treatments are provided for selectively stimulating receptors of the endocannabinoid system (ECS). The formulations include non-cannabis, plant-based agents from readily available herbs, spices and other flavonoid-containing plants. The formulations and treatments can be designed to modulate the ECS so as to achieve a variety of health and wellness effects without incurring various undesirable limitations associated with cannabis. Treatments can be developed rapidly by selecting plant agents that mimic ECS effects associated with established medical agents.

9 Claims, 1 Drawing Sheet

MODULATING THE ENDOCANNABINOID SYSTEM TO ACHIEVE DESIRED HEALTH OR WELLNESS EFFECTS

CROSS-REFERENCE TO RELATED APPLICATION

This application is a continuation of U.S. patent application Ser. No. 15/442,411, entitled, "MODULATING THE ENDOCANNABINOID SYSTEM TO ACHIEVE DESIRED HEALTH OR WELLNESS EFFECTS," filed on Feb. 24, 2017, which is a non-provisional of U.S. Provisional Application No. 62/301,219, entitled, "ENDOCANNABINOID TONING USING HERBS TO STIMULATE CB1 AND CB2 RECEPTORS AND INHIBIT THE UPTAKE OF THE FATTY ACID AMID HYDROLASE AND MONOACYLGLYCEROL," filed on Feb. 29, 2016. The contents of the above-noted application is incorporated by reference herein as if set forth in full and priority to this application is claimed to the full extent allowable under U.S. law and regulations.

FIELD OF THE INVENTION

The present invention relates generally to modulating (e.g., controlling or influencing) the endocannabinoid system to achieve desired health or wellness effects and, in particular, to the use of non-cannabis, plant-based agents (e.g., herbs and spices or, more generally, plants containing flavonoids) to selectively stimulate endocannabinoid receptors to achieve the desired effects.

BACKGROUND OF THE INVENTION

In recent years, considerable research has been directed to understanding the endocannabinoid system (ECS) and its effects on health and wellness. Much of this research has been inspired by reports of various benefits associated with cannabis, some of which have been further supported by scientific research. Among the more well-documented effects of cannabis are pain relief, appetite regulation and enhancing certain immune system functions. However, users have also reported that cannabis is effective in treating a variety of health problems such as glaucoma, anxiety, various types of seizers and cancer. While research continues to establish many of these claims, researchers are increasingly recognizing that the ECS has a broad range of effects on health and wellness.

Unfortunately, this research and broader acceptance of ECS-based treatments has been impacted by the association of the ECS with cannabis. The legal status of cannabis varies from jurisdiction-to-jurisdiction due to concerns about the recreational use of marijuana. In the United States, medical marijuana or recreational marijuana have now been legalized in many states, but marijuana is still illegal under federal laws and in many states. As a result, the ability of researchers to obtain funding and conduct research has been limited. Moreover, the health benefits of cannabis have been politicized in connection with legalization campaigns, leading to both exaggerated or premature claims of efficacy and unwarranted blanket claims of fraud and danger. The development and acceptance of the underlying science has suffered as a consequence.

DESCRIPTION OF THE INVENTION

The present inventor has recognized, and established through extensive research, that the ECS is a fundamental regulation system of the human body and other animals including mammals, birds and fish. Indeed, the inventor's research indicates that the ECS is not merely associated with various health and wellness effects, but exerts substantial control over many of the body's systems, including the central nervous system and organ systems. The ECS is thus in a position to influence every or nearly every system, organ and cell in the body and to address a vast assortment of conditions that are ultimately related to disregulation. In short, the ECS is a fundamental system of the body for action, control and feedback.

Moreover, the present inventor has recognized and established that the ECS can be modulated by influencing cannabinoids at ECS receptors, and the reported health and wellness benefits associated with cannabis are not limited to cannabis-based phytocannabinoids or synthetic cannabinoids and, specifically, are not limited to cannabis constituents such as tetrahydrocannabinoid (THC) or cannabidiol (CBD). Rather, the ECS is highly dependent on plant-based resources that may not be available in appropriate amounts or ratios in modern diets. Such resources can be provided by appropriate delivery mechanisms, e.g., for ingestion, inhalation or other delivery, to invoke desired responses by the ECS. That is, by administering appropriate dosages of certain plant-based agents in appropriate ratios, a broad array of health and wellness effects can be achieved.

In particular, the operation of the ECS is associated with endocannabinoid receptors, including the receptors CB1 and CB2. These receptors receive the endogenous neurotransmitters or endocannabinoids anandamide (AEA) and 2-archidonoylglucerol (2-AG). When cannabis is used, these receptors receive phytocannabinoids, including THC and CBD. The present invention is based in part on modulating the uptake or binding of cannabinoids by the receptors including the amount of uptake and the ratio of uptake. In this regard, the invention can operate free from using cannabis products and associated cannabis-based phytocannabinoids, which are problematic from a legal perspective as well as due to certain psychoactive effects. Rather, the invention can utilize other plant-based phytocannabinoids, which influence endocannabinoids and provide cannabinoid agonists, inhibitors, or antagonists, to stimulate the desired endocannabinoid system response. A variety of effects can thus be achieved, including replication of effects otherwise associated with the cannabis-based phytocannabinoids or other medicines.

A number of factors may affect transmission of neurotransmitters such as the cannabinoids across a synaptic cleft from the presynaptic side of the synapse to the post-synaptic side or receptor stimulation. These include the amount of the neurotransmitter that is released from the presynaptic side or otherwise available at the synaptic cleft, the amount of time that the neurotransmitter is active in the synaptic cleft before it is either metabolized by enzymes or reabsorbed by the presynaptic side (re-uptake), and the propensity of the receptors to bind to the neurotransmitters. Stimulation of the desired effects is also affected by antagonists which block the receptors normally stimulated by endocannabinoids or agonists. The plant-based agents of the present invention are believed to stimulate the receptors (CB1 and CB2) by increasing the amount of cannabinoids available at the endocannabinoid receptors and selectively increase binding of the cannabinoids by inhibiting degradation of the cannabinoids at the synaptic cleft by enzymes. Specifically, the plant-based agents provide the body with resources, e.g., cannabinoids, inhibitors or precursors, associated with production and availability of various cannabinoids or inhibitors.

With regard to inhibitors, certain of the plant-based agents are believed to enhance the effect of inhibitors for fatty acid amide hydrolase (FAAH) (that metabolizes AEA or other cannabinoids at the CB1 receptor) (CB1 uptake inhibitor) and monoacylglycerol lipase (MAGL) (that metabolizes 2-AG or other cannabinoids at least at the CB2 receptor) (CB2 uptake inhibitor). However, it is believed that any formulations effective to modulate stimulation of the endocannabinoid receptors, whether by supplying cannabinoids (e.g., endocannabinoids, agonists or antagonists) for binding at the CB1 and CB2 receptors (CB1 and CB2 effectors) or by inhibiting the breakdown of the cannabinoids at the CB1 and CB2 synaptic clefts (CB 1 and CB2 uptake inhibitors), or otherwise affecting the stimulation or relative stimulation of the endocannabinoid receptors including the CB1 and CB2 receptors, could be utilized to achieve desired effects, and desired effects may be achieved by influencing one or more factors affecting receptor stimulation. For example, certain effects may be obtained by utilizing only a CB1 or CB2 effector, or by utilizing only a CB1 or CB2 uptake inhibitor (e.g., so as to increase binding of AEA or 2-AG).

Particularly effective results have been achieved by controlling the ratio of the stimulation of the CB1 receptor to the stimulation of the CB2 receptor. The stimulation of the CB1 receptor can be achieved, for example, by one or both of a CB1 effector and a CB1 uptake inhibitor (e.g., an FAAH inhibitor) and the stimulation of the CB2 receptor can be achieved, for example, by one or both of a CB2 effector and a CB2 uptake inhibitor (e.g., an MAGL inhibitor). Ratios of less than 4:1 for the CB1 stimulation to the CB2 stimulation, for example, about 2:1 to 1:1, generally correspond to the effects associated with indica strain of cannabis. Ratios of greater than 4:1, for example, 8:1 to 10:1 generally correspond to the effects of the sativa strain of cannabis. The plant-based agents of the present invention can also mimic the ECS effects of other established medicines or treatments. The effects can further be enhanced by stimulating the endocrine channel. All of this can be accomplished using agents present in herbs, spices or other flavonoid-containing plants that are quite common and readily available in various geographies.

In accordance with one aspect of the present invention, a process is provided for modulating the ECS to achieve desired health and wellness effects. The process involves administering one or more non-cannabis, plant-based agents to a subject (e.g., by ingestion or inhalation or transdermally) in a dosage sufficient to produce at least one of: a first stimulation of first targeted endocannabinoid receptors, such as CB1 receptors, by first cannabinoids; and a second stimulation of second targeted endocannabinoid receptors, such as CB2 receptors, by second endocannabinoids. For example, the plant-based agents may include first plant-based agents having CB1 effectors (e.g., precursors or other resources derived from white onion or turmeric) and/or CB1 uptake inhibitors, for example, precursors or other resources, for promoting the effects of FAAH inhibitors (e.g., derived from red clover). The plant-based agents may further include second plant-based agents having CB2 effectors (e.g., from licorice) and/or CB2 uptake inhibitors, for example, for promoting MAGL inhibitors (e.g., derived from red sage). The process may further involve stimulating the endocrine channel by administering a plant-based stimulant such as guarana. Many more examples of the effectors, inhibitors and stimulants are provided below. These agents may be used in precisely controlled dosages/ratios to achieve various effects such as sativa-like effects (e.g., appetite control, affecting tolerance to alcohol or marijuana, increased energy and focus), indica-like effects (mood enhancement, pain relief, relaxation, sedation, calming, and anti-anxiety) and other effects. Many other effects are possible, some of which are discussed below.

In accordance with another aspect of the present invention, a composition is provided for use in modulating the ECS of a subject to achieve a desired health or wellness effect. The composition includes one or more first non-cannabis, plant-based agents in a dosage sufficient to produce at least one of: 1) a first stimulation of first endocannabinoid receptors by a first endocannabinoid; and 2) a second stimulation of second targeted endocannabinoid receptors by a second cannabinoid. The first and/or second stimulations may be induced by effectors or inhibitors, and may be provided in a desired ratio to achieve the desired effect. The composition may be provided, for example, in the form of a pill, a tea, a vape, or a cream.

In accordance with another aspect of the present invention, a process is provided for developing plant-based formulations for controlling the ECS to achieve desired health or wellness effects. As noted above, considerable research has been conducted related to the medical use of cannabis. Other medicines have been found to produce desired effects at least in part due to stimulation of ECS receptors. It has been found that these effects can be replicated by appropriate administration of agents to control cannabinoid uptake, thereby leveraging the research into medical cannabis and other medicines to accelerate development of non-cannabis, plant-based treatments. The associated process is initiated by identifying an application of a medical agent to treat a condition. For example, a given condition may be treated with a particular strain of medical cannabis, e.g., sativa or indica. The THC/CBD ratio of that strain can then be determined. For example, indica strains may have a ratio on the order of 1:1 whereas sativa strains may have a ratio on the order of 8:1.

An effect of the medical agent or ECS receptors associated with the medical agent may then be determined. For example, in the case of medical marijuana, the THC/CBD (or CB1/CB2) ratio may be determined. One or more subjects (e.g., a statistically and medically meaningful pool of subjects) may then be administered at least one or more first plant-based agents, different than the medical agent, where the first agents are associated with one or more plant influences on uptake of one or more cannabinoids by targeted endocannabinoid receptors. In the case of a condition treated by medical cannabis, the ratio of first and second influences can have a predetermined relationship to the THC/CBD ratio of the medical cannabis strain. For example, the ratio may substantially match the THC/CBD ratio in an effort to reproduce the medical cannabis effect, or the ratio may be varied from the THC/CBD ratio to optimize the effect. The subjects can be monitored to verify the resulting effects and develop the treatment.

BRIEF DESCRIPTION OF THE DRAWING

For a more complete understanding of the present invention, and further advantages thereof, reference is now made to the following detailed description, taken in conjunction with the drawing, in which.

DETAILED DESCRIPTION

I. The ECS System

The present invention is based in part on the recognition that the ECS is a fundamental system for regulating the body for many animals, that the ECS is resource-driven and that the ECS can be modulated to achieve a variety of health and wellness effects by providing the appropriate resources. While some such effects have been recognized in relation to cannabis, the present inventor has recognized that the range of effects is much broader than has been realized and the ECS can be modulated using non-cannabis agents. In the latter regard, it has been found that many herbs, spices and other flavonoid-containing plants include agents that function as, among other things, CB1 and CB2 effectors and uptake inhibitors. That is, the plant-based agents provide cannabinoids, uptake inhibitors, precursors or other resources that increase or decrease the amount/effectiveness of cannabinoids (e.g., endocannabinoids, agonists, antagonists) at the receptors (effectors) or that control how long cannabinoids remain active (e.g., via enzyme inhibitors or promoters) at the synaptic cleft (inhibitors).

Specifically, it has been recognized that the ECS plays a significant role in regulating many systems, organs, and cells of the body and can correct or remedy many conditions, especially conditions associated with disregulation. For example, the ECS has been found to exert substantial control over immune response, pain and mood, and regulation of eating/feeding/craving. While there are likely a variety of mechanisms by which the ECS exercises such control, the ECS appears to play a role in hormone release and organ control.

The control of the ECS involves endocannabinoid receptors including at least the CB1 and CB2 receptors. Various effects can be achieved by stimulating the CB1 receptors, by stimulating the CB2 receptors, or by controlling the relative stimulation of the CB1 and CB2 receptors. At a very general level, stimulating the CB1 receptors, or increasing the stimulation of the CB1 receptors in relation to the CB2 receptors, is generally associated with increased activity levels or up-regulation of the regulated system, such as increased focus, mental activity or increased immune response. These are generally sativa-like effects. On the other hand, increased stimulation of the CB2 receptors, or increased stimulation of the CB2 receptors in relation to the CB1 receptors, appears to be associated with reduced activity levels or down-regulation of the regulated system such as pain relief, reduced cravings or decreased immune response. These are generally indica-like effects.

In turn, there are at least two ways that plant-based agents can provide resources for modulating the operation of the endocannabinoid receptors including the CB1 and CB2 receptors. First, the receptors can be stimulated by effectors. Each of the receptors is adapted to bind with endocannabinoids. Specifically, the CB1 receptors prefer to bind with at least AEA and the CB2 receptors prefer to bind with 2-AG. Plant-based effectors are believed to include agents that increase or decrease the supply of cannabinoids (endocannabinoids, phytocannabinoids, agonists, antagonists) available at the synaptic cleft of the endocannabinoid receptors. Specific CB1 and CB2 effectors have been identified. Second, the receptors can be stimulated by uptake inhibitors. The uptake inhibitors generally decrease (but agents may also be employed that increase) the operation of enzymes on the cannabinoids at the synaptic cleft of the endocannabinoid receptors such that the availability and uptake of the cannabinoids is affected. Specific CB1 and CB2 uptake inhibitors have been identified that generally reduce the operation of enzymes and increase binding of cannabinoids by the receptors.

It should be appreciated that, while various agents are identified as effectors/inhibitors below, it is often difficult to distinguish these categories solely by monitoring effects (though the categories can ultimately be rigorously determined through research). For example, it may be difficult to distinguish a CB1 effector from a CB1 uptake inhibitor as each of these potentially increases the uptake of cannabinoids by the CB1 receptor. Further, some herbs contain flavonoids which affect both receptors. In addition, because many effects are associated with the ratio of CB1 stimulation to CB2 stimulation, it may be difficult to distinguish, for example, a CB1 effector from an agent that decreases the action of a CB2 uptake inhibitor (or otherwise increases the activity of a CB2 enzyme) or from a CB2 antagonist. The labels below thus reflect, in some cases, a best effort to categorize based on observations (where other research is unavailable).

It is also possible that the operation of the inhibitors could be reduced or avoided by certain agents, e.g., antagonists, so that the enzymes would be more effective or stimulation of the receptors would be otherwise reduced (due to reduced binding of effective cannabinoids at the receptors). Generally, though, stimulation of the CB1 receptors is increased by increasing the supply of CB1 effectors and/or CB1 uptake inhibitors, or stimulation is decreased by antagonists. Stimulation of the CB2 receptors is increased by increasing the supply of CB2 effectors and/or CB2 uptake inhibitors or stimulation is decreased by antagonists. Up-regulation is achieved by increasing stimulation of CB1 receptors over CB2 receptors and down-regulation is achieved by increasing CB2 receptor stimulation over CB1 receptor stimulation. Different effectors and uptake inhibitors, and different delivery systems, in some cases appear to target different receptors associated with different effects. In addition, different delivery systems are associated with different effective dosages, different latencies or response times, and different duration of effects.

There are a number of other factors that may influence the effectiveness of the effectors and uptake inhibitors. For example, the effectiveness of certain formulations have been found to be enhanced by plant-based agents that stimulate the endocrine channel.

II. Agents

As noted above, a variety of desired health and wellness effects can be achieved in accordance with the present invention by using plant-based agents to selectively stimulate endocannabinoid receptors including the CB1 and CB2 receptors, and by using plant-based agents found to enhance these effects. The compositions described below may thus include one or more of a CB1 effector, a CB2 effector, a CB1 uptake inhibitor, a CB2 uptake inhibitor, and an endocrine channel stimulator. Further, in some cases, herbs contain flavonoids which have actions at both CB1 and CB2 receptors. Examples of each of these are provided below. It will be appreciated that these are all found in common plants. Further, a full set of influencers is readily available in almost any region of the world and these examples are not exhaustive.

A. CB1 Effectors

Based on research and observed effects, it has been recognized that the CB1 effectors set forth below increase cannabinoids available for binding at CB1 receptors. In particular, it is understood that, upon delivery to a subject, the CB1 effectors supply resources to enhance the availability of at least AEA (2-AG may be active at both CB1 and CB2 receptors) and/or AEA agonists that bind to the targeted CB1 receptors and produce effects similar to the endocannabinoid AEA. Examples include:

TABLE 1

| CB1 Effector | Flavonoid | Effect | Targeted Receptors or Systems |
|---|---|---|---|
| White Onion | Quercetin | Energy, Focus, Creative, Cell Apoptosis, Colon Cancer | CB1 |
| Turmeric | Curcumin | Energy, Focus, Creative, Strongly Anti-inflammatory | CB1 |
| Chili Pepper | Capsaicin | Energy, Causing Sweating, Internal Heat Feeling, Focus | CB1 + TRPV1 |
| Black Pepper | b-Caryophyllene | Energy, Antioxidant, Mood Enhancement, Cancer | CB1 |
| Tart Cherry | cyanidin delphinidin | Functions as both a CB1 and CB2 effector, also effects re-uptake | CB1/2 |

B. CB2 Effectors

Based on research and observed effects, it has been recognized that the CB2 effectors set forth below increase cannabinoids available for binding at CB2 receptors. In particular, it is understood that, upon delivery to a subject, the CB2 effectors supply resources to enhance the availability of 2-AG and/or 2-AG agonists that bind to the targeted CB2 receptors and produce effects similar to the endocannabinoid 2-AG. Examples include:

TABLE 2

| CB2 Effector | Flavonoid | Effect | Targeted Receptors or Systems |
|---|---|---|---|
| Licorice | 18b-Glycyrrhetinic Acid | Relaxing, Anti-anxiety, Calming | Downregulates CB1 |
| Turmeric | Curcumin | Energetic, Focus | CB2 |
| Black Pepper | b-Caryophyllene | Relaxing, Anti-anxiety | CB2 |
| Echinacea | dodeca-2E,4E,8Z,10Z-tetraenoic acid isobutylamide and dodeca-2E,4E-dienoic acid isobutylamide | Relaxing, Calming | CB2 |
| Tart Cherry | cyanidin delphinidin | Functions as both a CB1 and CB2 effector, also effects re-uptake | CB1/2 |

C. CB1 Uptake Inhibitors

Based on research and observed effects, it has been recognized that the CB1 uptake inhibitors set forth below inhibit the operation of the enzyme FAAH at the synaptic cleft of the CB1 receptor. As a result, the endocannabinoid AEA, as well as any AEA agonists, remain active for binding to the CB1 receptor for a greater time period. Examples include:

TABLE 3

| CB1 uptake inhibitor | Flavonoid | Targeted Receptors or Systems |
|---|---|---|
| Red Clover | Biochanin A | CB1 |
| White Onion/St. Johns Wort | Kaempferol | CB1 |

D. CB2 Uptake Inhibitors

Based on research and observed effects, it has been recognized that the CB2 uptake inhibitors set forth below inhibit the operation of the enzyme MAGL at the synaptic cleft of the CB2 receptor. As a result, the endocannabinoid 2-AG, as well as any 2-AG agonists, remain active for binding to the CB2 receptor for a greater time period. Examples include:

TABLE 4

| CB2 uptake inhibitor | Flavonoid | Targeted Receptors or Systems |
|---|---|---|
| Red Sage | Tanshinone IIA | CB2 |
| Celastraceae Family | Pristimerin | CB2 |

E. Endocrine Channel Stimulators

As set forth below, it has been found that the various formulations for modulating the ECS can be enhanced by including an endocrine channel stimulator. An example is provided below:

TABLE 5

| Stimulator | Flavonoid | Targeted System |
|---|---|---|
| Guarana | Catechins/Caffeine | Endocrine |

III. Delivery Systems

Many delivery systems are possible for making the agents available at the desired site, e.g., targeted endocannabinoid receptors. Different delivery systems, even for the same formulation, may produce different effects, have different efficacies, or have different effective times or durations. Without limiting the possible delivery systems, the following sections provide examples of delivery by pills, teas, vapes, and topical/transdermal systems. In addition, care must be taken to ensure that effectiveness is not impaired by barriers along the delivery pathway to the targeted site. For example, there is a greater barrier, associated with endothelial cells, for delivering agents from your digestive tract (e.g., pills, teas) to your neurology, than there is for delivering agents from your respiratory system (e.g., vapes) to your neurology. Agents delivered via the digestive track may have a longer lasting effect and require a larger dosage whereas agents delivered via the respiratory system may have a more immediate effect at a lower dosage.

A. Capsules

Capsules are filled with the desired agents, in the desired proportions, provided in powdered form. Preferably, the herbs are obtained from large herbal suppliers, such as Ecuadorian Rain Forest, LLC, and have certificates of authentication (COA's) for all herbs as well as determining any heavy metal content, contaminants, and also ensure flavonoid levels. Although various dosages can be utilized effectively, in some cases, the pills are produced such that a single pill includes dosage intended for approximately a 75 pound range such that a subject weighing up to 75 pounds would take 1 pill per treatment, a subject weighing 75-150 pounds would take 2 pills, etc.

B. Teas

Teas can be prepared by providing the desired herbs and spices, in the desired proportions, as raw or dried herbs or spices or as powders. Water and additional ingredients (e.g., flavorings) can be added to produce a tea for consumption by the subject.

C. Aroma Therapies a. Inhalable Aroma Therapies

Some aroma therapies are meant to be inhaled and can be consumed in a variety of devices including inhalable vaporization devices similar to what are used in the electronic cigarette market. Agents may be extracted from raw herbs and spices by using one part herbal formulation to three parts of a combination of 25% ethanol and 75% cold water. A vape can be created from the water soluble flavonoids which can easily be extracted from our herbal formulations. An amount of herbal material is measured (e.g., 100 g) and we consider this ¼ of our total extraction formulation. We then add ¼ ethanol (100%=100 ml) and ½ cold water (=200 ml). The water and the ethanol are poured over the herbal material and the herbal material is stirred until dissolved. This is let to stand for 2 hours and then strained. The liquid is then strained away from the remaining plant material. The liquid can be used in a variety of applications including but not limited to the active ingredient in a vape. The vape is created simply by combining the liquid extraction in an existing vape flavor or by custom building the vape. Best performance has been found by a base of vegetable glycerin, then adding flavoring at 20%, then adding the extraction at 10%. Further, this extracted liquid can be used to flavor aroma therapies b. Passive Aroma Therapies These combine the noted formulations with existing essential oils, something like Jasmine, that may or may not be intended to be actively inhaled, but may simply be breathed.

D. Lotions

The desired herbs and spices can be provided in a powdered form, as discussed above, in the desired proportions. The powder can then be mixed with base lotion ingredients selected to enhance absorption/penetration and provide other desired effects (moisturization, sunblock, etc.). For example, the base lotion ingredients may include aloe, shea butter, or coconut oil. The herb and spice powders may be mixed with the base lotion ingredients by adding herbal material to the lotions and mixing vigorously. The lotion can then be applied directly to an effected site or at a prescribed location for absorption into the bloodstream. Further, the same method of extracting the flavonoids can be used as in the method described for aroma therapies. The result is a water based liquid heavily saturated with flavonoids. This "oil" may be also added to lotions or other cosmetic products to produce desired effects. For instance, an acne creme may be supplemented with an oil which is targeted toward healing and anti-inflammation.

IV. Examples of Products/Treatments

A. Capsule-Based

1. Foundation Product

The Foundation Product is a core and general health product that may be taken on a continuing basis rather than as a remedial product. Foundation is targeted at giving the endocannabinoid system (ECS) the very basic and specific resources it needs to function properly. In particular, the Foundation product provides the raw materials to target both CB1 and CB2 receptors in several ways. Turmeric provides both the ability to stimulate CB1 receptors, and also in certain instance to block them. Black pepper contains a very powerful flavonoid called peperine that is both a CB1 and CB2 effector. These allow the body a better ability to up and down regulate the ECS even down to the cellular level. The Foundation product may thus comprise at least about 25% CB1 effector sources, at least about 25% CB2 effector sources, and may also include CB1 and CB2 uptake inhibitor sources and an endocrine stimulator.

Turmeric also contains plant flavonoids thought to be some of the best anti-inflammatory medications available. Red Clover is an FAAH uptake inhibitor (allowing more action at CB1), Ginger is a bit of an unknown but we feel performs well with turmeric and is a CB1 effector, and optional ingredient Shilajit appears to be a strong CB2 effector. Cocoa is a CB1 effector. Horseradish and Mucana Pruriens both provided needed resources. Horseradish is a natural source of NAPE which provides many endocannabinoids as it breaks down. Mucana Pruriens is a good source of L-Dopa and could provide a way to replenish dopamine.

Dosage: The dosages depend on the subject's weight and ability to absorb nutrients. In general, a dosage of product will be one capsule for every 75 pounds of body weight. So below 75 pounds=1 capsule; 75-150 take 2 capsule; etc. If the subject has issues with absorption, these can usually be addressed by 4 doses of the Gut Awake tea described below.

Duration: Foundation is our general health product and is targeted to provide the resources that are needed to properly fuel the ECS. The other products described below are for certain conditions. It is thus recommended to take the Foundation product on a daily basis and take the other products as needed. We understand vitamins and minerals to be something we need daily to function properly. In a similar fashion, it has been found that the ECS needs daily resources.

Ingredients: Turmeric (15-25%), Black Pepper (15-25%), Red Clover (10-20%), Ginger (10-20%), Guarana (10-20%), Cocoa (2-5%), Horseradish (2-5%), Mucana Pruriens (2-5%). Purpose: General overall body regulation.

2. Relief

Some of the biggest health issues today are 1) an inability for the general population to handle daily aches and pains well 2) resulting in a huge overabundance of opiates causing addiction and major health issues.

We require very basic and specific resources to function properly. Many individuals' bodies hurt because they don't have the proper nutrition. In our ECS, we require these resources to simply fire neurons. In a CNS event which involved any other neuro process (non ECS), neurons fire by first being engaged at a receptor by a transmitter, then the neuron releases all the transmitters it has stored (within that system) which propagates the event. In an ECS firing, neurons behave differently. They must manufacture or synthesize the needed resources to prolongate and ECS event "on demand." If resources are not available the event will fail. Further, this simple description fully explains and describes how the ECS, even at neuronal firing, is a more basic and fundamental system than the CNS. Due to changes in how we process and prepare our food, and the industrial processes most food is put through, most individuals lack these very important plant-based flavonoids. Without these resources we break down and break down along paths defined by our genetics. If the needed ECS resources are not available, the body will attempt to regulate as well as possible with limited resources, but regulation will be sub-optimal and will be executed via alternate pathways. These would be different for each individual given that we are all genetically diverse. However, these would lump into large categories of bodily disregulation. Auto-immunes, cancers, pain management, seizures, mood disorders (we should all function in a manageable range) all are viewed as states of disregulation under the invention and science described herein.

The Relief product provides the very raw resources to enable your ECS to work better at the central nervous system level. In particular it stimulates the CB1 and CB2 receptors and more heavily influences the CB2 receptor. This results in better pain management while avoiding the addictive properties of certain conventional pain management approaches. For example, the Relief product may contain at least 20% CB1 effector sources and at least 30% CB2 effector sources, and may further include CB1 and CB2 uptake inhibitors and an endocrine stimulator. By providing your body the resources it needs, it handles the pain response far better. In our understanding of how the body works through our ECS lens, we view pain as a response and a cue. You get pain to cue you, and your brain, that there is an issue, and a serious one! However, because we are all resource deprived in the ECS, we do not have the proper resources to modulate this response. In some cases we are constantly in "pain" because we do not have the resources levels to turn off the pain cues. Where do we hurt? We hurt in areas of ongoing repair/damage/trauma. It has been found that just by providing the proper ECS resources, the body is able to far better manage this response.

The Relief product contains white onion and red clover which very specifically target the CB1 neuroreceptors, and further contains red sage and licorice which target the CB2 neuroreceptor.

Dosage: The dosages depend on the subject's weight and ability to absorb nutrients. In general, a dosage of product will be one capsule for every 75 pounds of body weight. So below 75 pounds=1 capsule; 75-150 take 2 capsule; etc. If the subject has issues with absorption, these can usually be addressed by 4 doses of the Gut Awake tea.

Duration: The Relief product can be taken as needed for pain relief.

Ingredients: White Onion (15-25%), Red Clover (15-25%), Licorice (15-25%), Red Sage (15-25%), Guarana (5-15%), Horseradish (3-5%), Cocoa (3-5%), Mucana Pruriens (3-5%). Purpose: Pain relief 3. Sleep Without regenerative Sleep your body cannot properly rebuild and heal. Many studies have shown the tremendous benefits of a good night's rest. Sleep is a body regulation issue and is heavily if not totally regulated by the ECS. In fact, a buildup of something called oleoamide, an endocannabinoid, in your spine will quickly induce sleep. The sleep product is a deeper tuning of the Relief product and provides similar benefits. It puts your body in a relaxed and pain-free state allowing a deep and regenerative sleep. The Sleep product may contain at least 20% CB1 effector sources and 35% CB2 effector sources, and may further contain CB1 and CB2 uptake inhibitors and an endocrine stimulator.

Dosage: The dosages depend on the subject's weight and ability to absorb nutrients. In general, a dosage of product will be one capsule for every 75 pounds of body weight. So below 75 pounds=1 capsule; 75-150 take 2 capsule; etc. If the subject has issues with absorption, these can usually be addressed by 4 doses of the Gut Awake tea.

Duration: The Sleep product can be taken on a regular basis at bedtime or as needed to induce sleep.

Ingredients: White Onion (10-20%), Red Clover (15-25%), Licorice (20-30%), Red Sage (15-25%), Guarana (5-15%), Horseradish (3-5%), Cocoa (3-5%), Mucana Pruriens (3-5%). Purpose: Pain relief and sleep aide.

4. Fit

At times we all need that boost of energy and creativity. The Fit product is designed to provide just that. It provides energy, creativity, and focus. Cnidium Morrieri is the main herb in this formulation and is believed to be a strong CB1, endocrine, and GABA effector. The Fit product preferably includes at least 25% CB1 effector sources. Further, turmeric and black pepper are used which, in combination, offer strong neuroprotective properties and research says can stimulate brain cellular growth. The Fit product is designed to be energetic, mood uplifting, and thought provoking.

Dosage: The dosages depend on the subject's weight and ability to absorb nutrients. In general, a dosage of product will be one capsule for every 75 pounds of body weight. So below 75 pounds=1 capsule; 75-150 take 2 capsule; etc. If the subject has issues with absorption, these can usually be addressed by 4 doses of the Gut Awake tea.

Duration: The Fit product can be taken on a regular basis or as needed.

Ingredients: Cnidium Monnieri (25-35%), Black Pepper (25-35%), Turmeric (10-20%), Guarana (10-20%), Horseradish (3-5%), Cocoa (3-5%), Mucana Pruriens (3-5%). Purpose: Energy, focus, alertness 5. Weight The Weight product is very specifically designed for obesity, pre-obesity, immune balance, and type II diabetes. The Weight product includes olive leaf and kale to very specifically target Omega 3 intake. Obesity is strongly tied to Omega 6 resources being too high. These resources break down into endocannabinoids and cause the ECS to be perpetually stimulated in the hypothalamus. This creates a situation of almost perpetual hunger. The Weight product attempts to bring this ratio back into balance by providing the body with easily accessible Omega 3 resources.

Dosage: The dosages depend on the subject's weight and ability to absorb nutrients. In general, a dosage of product will be one capsule for every 75 pounds of body weight. So below 75 pounds=1 capsule; 75-150 take 2 capsule; etc. If the subject has issues with absorption, these can usually be addressed by 4 doses of the Gut Awake tea.

Duration: The Weight product can be taken on a regular basis or as needed.

Ingredients: Kale (20-40%), Black Pepper (20-50%), Olive Leaf (25-50%), Cnidium Monnieri (15-50%), Red Clover (20-40%), Turmeric (15-25%).

Purpose: Weight control (longer term).

B. Teas

The teas are designed for more specific ailments and conditions. It is recommended that the teas be used with the capsule based products.

1. Fit

A very energetic tea design to inspire focus, energy, and creativity. It is a nootropic which is designed to help your brain function better. It contains turmeric which is a known brain nerve growth stimulant.

Dosage: 5 g up to 15 g. Greater dosage will result in greater effects.

Duration: As needed

Ingredients: Cnidium Monnieri (25-35%), Black Pepper (25-35%), Turmeric (10-20%), Guarana (10-20%), Horseradish (3-5%), Cocoa (3-5%), Mucana Pruriens (3-5%).

Purpose: Energy, focus, alertness

2. Experience

A tea designed to stimulate the libido and awaken the senses. It also provides clarity, focus, and a minor energy boost. It will increase skin sensitivity and lower inhibitions. Goes well with a minor amount of alcohol as an aphrodisiac.

Dosage: 5 g up to 15 g. Greater dosage will result in greater effects. Ingredients: Black Pepper (15-25%), Mucana Pruriens (10-20%), Frankincense (10-20%), Olive Leaf (10-20%), Cnidium Monnieri (5-15%), Maca (5-15%), Red Clover (5-15%), Guarana (5-15%), Shilijat (5-15%), Ginger (3-5%).

Purpose: Aphrodisiac, provides increased skin sensitivity.

3. Relief

A tea-based complement to the Relief capsules product. This tea will assist with daily pain. It is also relaxing and calming. A very good night time tea and sleep aide as well as providing pain relief.

Dosage: 5 g up to 15 g. Greater dosage will result in greater effects.

Duration: As needed

Ingredients: Peppermint (15-25%), Red Clover (15-25%), Licorice (15-25%), Red Sage (15-25%), Guarana (5-15%), Horseradish (3-5%), Mucana Pruriens (3-5%), Cocoa (3-5%). Purpose: Pain relief 4. Stomach A tea designed to assist with relief from an upset stomach. It contains herbs specifically designed to address stomach inflammation and also to calm and soothe the stomach. It also contains ginger which is used in a lot of prescription anti-nausea medications.

Dosage: 5 g up to 15 g. Greater dosage will result in greater effects.

Duration: As needed Ingredients: Peppermint (10-20%), Red Clover (10-20%), Ginger (10-20%), Black Pepper (10-20%), Turmeric (10-20%), Sage (10-20%).

Purpose: Upset stomach relief

5. Allergy

A tea designed to assist with allergies and colds. This tea contains herb decongestants and antihistamines and is a very powerful aide in dealing with allergy symptoms.

Dosage: 5 g up to 15 g. Greater dosage will result in greater effects.

Duration: As needed

Ingredients: Peppermint (7-15%), Red Clover (7-15%), Ginger (7-15%), Black Pepper (7-15%), Turmeric (7-15%), Sage (35-50%).

Purpose: Allergy relief

6. Gut Awake

A very specific tea design to restart the gut. Most of us, due to diet, have intestinal scarring. As a population about 50% of our diet is gluten. Gluten is known to cause intestinal scarring and this degrades our ability to absorb our food and to get proper feedback about our nutrient intake. This scarring results in a surface that cannot absorb properly. It is believed this is an underlying cause of many of the digestive issues we see today including Crohn's and IBS. This tea must be consumed carefully as the purpose is to stimulate the CB1 neuroreceptors in the digestive system. This tea should only be taken in 2 to 4 back to back doses usually 12 hours apart.

Dosage: 5 g up to 15 g. Greater dosage will result in greater effects.

Duration: As needed Ingredients: White Onion (25-40%), Ginger (25-40%), Cayenne (25-40%).

Purpose: Will re-start gut and assist with IBS, Crohn's, help re-build probiotics.

C. Aroma Therapies

The inventive "vapable" aroma therapies or "I"nhalable "A"orma "T"herapies (IAT) will affect the body much quicker than a tea or a capsule and in much smaller concentrations. However, the duration of the effect will be less than a capsule or a tea. IAT's have a strong place in many health instances including pain relief, anti-anxiety, mood improvement, energy, creativity.

1. Fit

An energetic IAT designed to inspire focus, energy, and creativity. It has higher nootropic properties as an IAT but shorter duration.

Ingredients: Cnidium Monnieri (25-35%), Black Pepper (25-35%), Turmeric (10-20%), Guarana (10-20%), Horseradish (3-5%), Cocoa (3-5%), Mucana Pruriens (3-5%).

Purpose: Energy, focus, alertness

2. Focus

Focus is different than Fit, but has a similar goal. Focus provides a less energetic Fit. It also has high nootropic properties but somewhat short duration.

Ingredients: Coffee (10-20%), Quinoa (20-30%), Peppermint (25-35%), Red Clover (5-15%), Guarana (5-15%), Licorice (10-20%), Cocoa (5-15%), Shilij at (10-20%).

Purpose: provides stimulation and focus.

3. Relief

An IAT complement to our relief capsules product. This IAT will assist with daily pain. It is also relaxing and calming. A very good night time tea and sleep aide as well as providing pain relief.

Ingredients: Peppermint (15-25%), Red Clover (15-25%), Licorice (15-25%), Red Sage (15-25%), Guarana (5-15%), Horseradish (3-5%), Mucana Pruriens (3-5%), Cocoa (3-5%). Purpose: Pain relief 4. Herbal Nicotine Replacement We have used the ECS model to "mimic" the effects of nicotine using herbs. The herbal nicotine replacement (HNR) products will replace nicotine with no or minimal withdrawal, cravings, anxiety, or weight gain. The HNR products can be flavored.

Ingredients: Cocoa (10-25%), Guarana (25-45%), Red Clover (10-25%), Sage (25-45%), Mucana Pruriens (1-3%), Horseradish (1-3%) Purpose: replaces nicotine.

D. Skin Creams

Early testing has shown tremendous promise with our Relief formulation, put in a lotion or cream, and applied to damaged or injured skin. Early testing with psoriasis has shown very positive results.

E. Pet Medications

Early testing has shown that our herbal formulations and in particular Foundation and Relief have shown promise in treating pain and inflammation in animals.

V. Rapid Development of Treatments

From the foregoing discussion, it is clear that the plant-based agents of the present invention can stimulate targeted receptors, either by increasing binding to endocannabinoids or to other cannabinoids. Research into the effects of established and investigated medical agents has yielded considerable information concerning the pathways by which the medical agents function and, more generally, observed effects of these medical agents. In many cases, these effects have included influencing the binding of neurotransmitters to receptors. The present inventor has recognized that these are not incidental effects, but rather involve tapping into fundamental regulatory systems of the body. This opens a significant research vector for developing treatments for many and varied health and wellness problems. The inventor has already been able to use this research vector to develop a number of non-cannabis, plant-based treatments.

One example of this relates to reported effects of medical cannabis. In particular, different strains of medical cannabis have been associated with different effects. For example, without attempting an exhaustive listing, sativa strains have been associated with decreased appetite, affected tolerance to alcohol, enhanced energy and focus, and enhanced mood, and indica strains have been associated with pain relief, calming, sedation and anti-anxiety. Moreover, the THC to CBD ratio of these strains, which correspond to the CB1 to CB2 stimulation ratio, is often known or can be determined or estimated (indeed, in jurisdictions where medical or recreational cannabis is legal, this ratio is often advertised). As noted above, such CB1 to CB2 stimulation ratios can be achieved by appropriate dosages including appropriate ratios of non-cannabis, plant-based agents.

Another example relates to treating nicotine dependence or addiction. Nicotine craving has been associated with the ACH channel involving the neurotransmitter acetylcholine and its receptor. The inventor has learned that nicotine cravings can be reduced by administering a non-cannabis, plant-based composition that stimulates the ACH channel. Specifically, formulation involving a perceived ACH effector, such as red sage, and/or a perceived ACH inhibitor, such as guarana, have been found effective.

Yet another example relates to treatment to assist in reducing obesity. The hypothalamus is involved in generating signals associated with "hunger" and "fullness." Under certain conditions related to the need for resources, the hypothalamus cues the digestive tract to release ghrelin which results in the perception of hunger. Then, as you eat, the resource levels adjust eventually causing the hypothalamus to control the digestive tract to release leptin which results in the sensation of fullness. Some treatments have targeted these cue systems.

It has been recognized that the resources associated with these triggers involve ECS resources including linoleic acid that we get from a variety of foods. However, the linoleic acid is broken down by omega 3 and omega 6 fatty acids. The omega 6 path creates ECS resources and the omega 3 path creates other needed resources. Unfortunately, modern diets include a drastically different ratio of omega 3 to omega 6 fatty acids than natural or traditional diets, resulting in misregulation of hunger and fullness signals. In accordance with the present invention, non-cannabis, plant-based formulation can be administered to subjects to bring omega 3 and omega 6 back into balance and otherwise promote digestive health.

Figure 1:
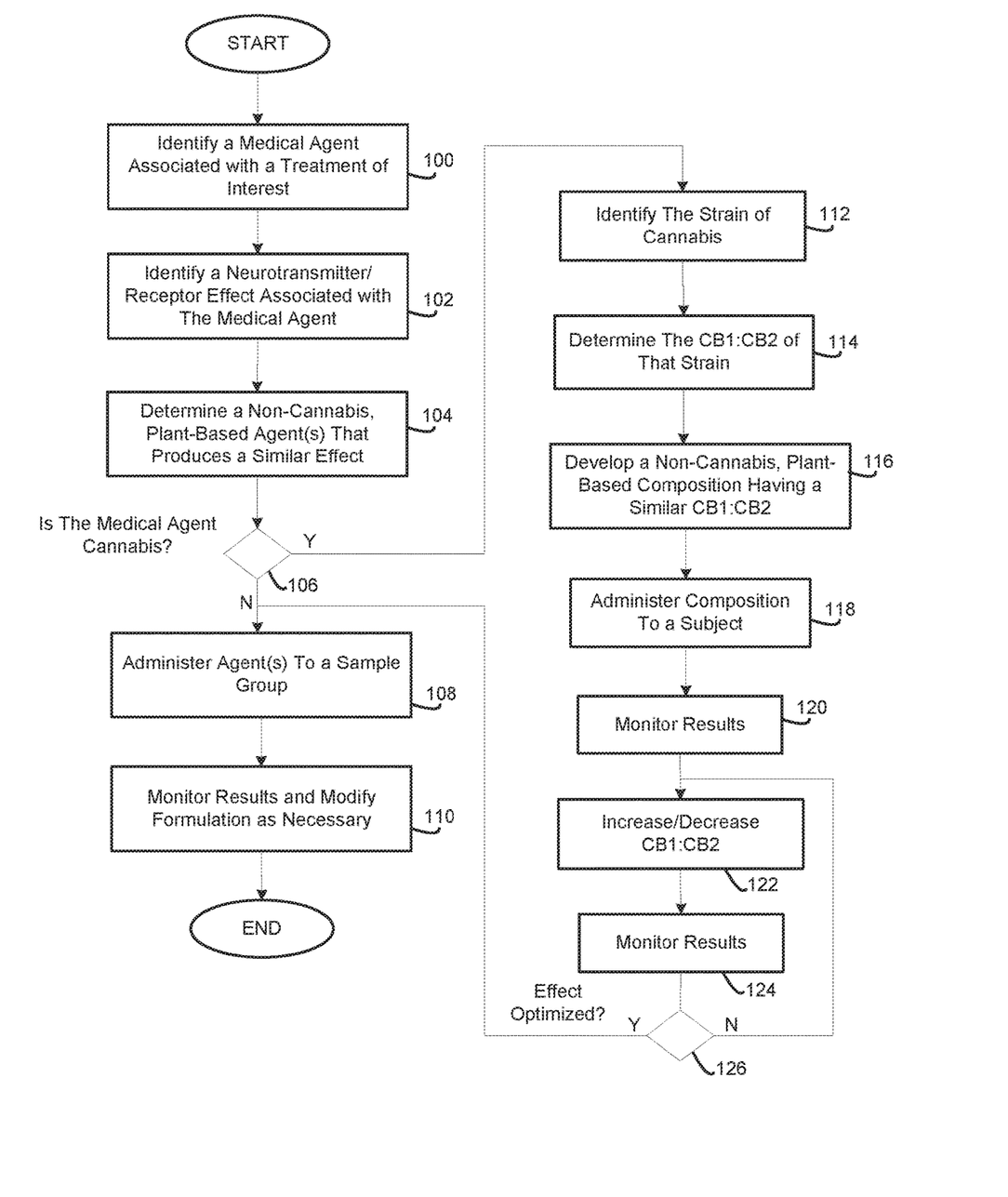
FIG. 1 is a flowchart showing a rapid development process in accordance with the present invention.

Rapid development of non-cannabis, plant-based treatments, by leveraging the experience of medical cannabis or other established treatments, can thus proceed as follows, and as shown in the flow chart of FIG. 1. The illustrated process is initiated by identifying (100) a medical agent associated with a treatment of interest, e.g., a medical cannabis treatment or treatment for nicotine addiction. A neurotransmitter and associated receptors associated with the medical agent can then be identified (102). For example, nicotine treatments may involve the ACH channel and medical cannabis may be associated with CB1 and CB2 receptor effects. Based on the observed or known effects, a non-cannabis, plant-based agent or agents can be determined (104) that yield similar effects.

Thus, for example, if the medical agent is medical cannabis (106), the strain of the cannabis can be identified (112) and a THC:CBD or CB1:CB2 ratio of the strain can be determined (114). The model of the present invention can then be used to develop (116) a non-cannabis, plant-based composition having a similar ratio of stimulating the CB1 receptors to stimulating the CB2 receptors (CB1:CB2). Generally, a CB1:CB2 of less than 4:1, for example, 2:1 to 1:1 produces an indica-like effect whereas a CB1:CB2 of greater than 4:1, for example, 8:1 to 10:1 produces a sativa-like effect.

The resulting composition can then be administered (118) to a subject, e.g., by pills or a vape. The results can be monitored (120) to verify the expected result. Moreover, the CB1:CB2 of the formulation can then be incrementally increased/decreased (122) and the results again monitored (124) to hone in on the optimal effect (126), which may be slightly different than the CB1:CB2 of the medical cannabis that originally established the effect. Indeed, the inventive technique allows for precisely controlling the ratios of agents to identify, to a high degree of precision, the ideal CB1:CB2.

In any event, the non-cannabis, plant-based formulation can then be administered (108) to a sample group. The sample group can be selected in accordance with accepted practices to be statistically and medically significant. The results can then be monitored (110) and the formulation can be modified as necessary. In this manner, non-cannabis, plant-based treatments can be rapidly developed by leveraging known treatments as well as the emerging knowledge base of non-cannabis, plant-based agents.

VI. Treatment Examples

1. Example 1—Pain Relief

A pain relief formulation based on non-cannabis, plant based agents was administered to a female subject. The subject was a 35 year old woman experiencing chronic pain due to a 2-level spinal fusion in her neck. The subject was experiencing an 8-9 level pain daily and was using chiropractic and other homeopathic methods of pain relief.

A non-cannabis, plant based formulation was developed to relieve the pain. It was anticipated that an indica type effect would likely yield pain relief. Accordingly, the formulation was design to effect a CB1:CB2 ratio of about 1:1. The specific formulation was white onion, red clover, red sage, licorice, guarana, horseradish, and mucana pruriens. Ratios are associated with White Onion/Red Clover (CB1 effectors) and Red Sage/Licorice (CB2 effectors). The formulations were provided in capsule form.

The subject weighed approximately 120 lbs and took 2 capsules per treatment, twice per day. Within 1 hour, the subject's pain had lessened and within 2 hours the subject had dropped to a 1 on the pain scale. The subject is continuing treatment (over 1 year) with subsequent pain relief.

2. Example 2—Foundation Product and General Body Regulation

A 120 lb woman was having issues with mood and regular periods. She began taking the Foundation product as per the dosage instruction on the product label. Her immediate observations were (within first 3 days): Mood improvement and appetite somewhat decreased. Within 4 months of taking the product the woman began having regular periods, which she had never had in her life. Further, over the course of the last year the periods have continued on a regular basis, in fact almost to the day.

The foregoing description of the present invention has been presented for the purpose of illustration and description. Furthermore, the description is not intended to limit the invention to the form disclosed herein. Consequently, variations and modifications commensurate with the above teachings, and skill and knowledge of the relevant art are within the scope of the present invention. The embodiments described herein above are further intended to explain best modes known of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

The invention claimed is:

1. A method for developing a plant-based formulation to achieve a health treatment which has been previously achieved by a cannabis-based agent, the method comprising:
   identifying the health treatment effect achieved by the cannabis-based agent, wherein the health treatment includes at least one of controlling immune response, pain relief, sleep regulation, controlling mood, regulation of eating, relief from an upset stomach, treating nicotine dependence, and allergy relief, and wherein the cannabis-based agent causes an endocannabinoid system (ECS) receptor effect which results in the health treatment effect;
   identifying the ECS receptor effect caused by cannabis-based agent, wherein the ECS receptor effect includes that the cannabis-based agent acts as at least one of a CB1 effector, a CB2 effector, a CB1 uptake inhibitor, a CB2 uptake inhibitor, or a TRPV1 effector;
   determining one or more non-cannabis plant-based agents which produce the ECS receptor effect, wherein the non-cannabis plant-based agent(s) include at least one of a source selected from the group consisting of a source of quercetin, a source of curcumin, a source b-caryophyllene, a source of 18b-glycyrrhetinic acid, a source of biochanin A, a source of Tanshinone IIA, and mixtures thereof; and
   formulating a plant-based formulation having an effective amount of the non-cannabis plant-based agents to produce the ECS receptor effect.

2. The method of claim 1, wherein the source of quercetin is white onion, the source of curcumin is turmeric, the source of b-caryophyllene is black pepper, the source of 18b-glycyrrhetinic acid is licorice, the source of biochanin A is red clover, and the source of Tanshinone IIA is red sage.

3. The method of claim 1, wherein the ECS receptor effect includes that the cannabis-based agent acts as both a CB1 effector and a CB2 effector.

4. The method of claim 3, wherein the non-cannabis plant-based agents include at least one of:
   a source of quercetin, or a source of curcumin, or both; and
   a source of b-caryophyllene, or a source of 18b-glycyrrhetnic, or both.

5. The method of claim 4, wherein the source of quercetin is white onion, the source of curcumin is turmeric, the source of b-caryophyllene is black pepper, and the source of 18b-glycyrrhetinic acid is licorice.

6. The method of claim 3, wherein the plant-based formulation includes at least one compound selected from the group consisting of guarana, ginger, cocoa, horseradish, mucana pruriens, cnidium monnieri, peppermint, and mixtures thereof.

7. The method of claim 1, further comprising:
   identifying if the cannabis-based agent acts as an endocrine channel stimulator; and
   determining at least one plant-based agent that acts as an endocrine channel stimulator, and wherein the plant-based formulation formulated includes the plant-based agent that acts as an endocrine channel stimulator.

8. The method of claim 7, wherein the plant-based agent that acts as an endocrine channel stimulator is guarana.

9. The method of claim 1, wherein:
   the method further comprises identifying a strain type for the cannabis; and
   the step of identifying an ECS receptor effect includes determining the ratio of stimulating CB1 receptors to stimulating CB2 receptors for the strain type.

* * * * *